United States Patent [19]

Johnson

[11] 4,010,820

[45] Mar. 8, 1977

[54] ACOUSTIC EAR MOLD FOR HEARING AID

[76] Inventor: Rubein V. Johnson, 2432 Court St., Muskogee, Okla. 74401

[22] Filed: Aug. 1, 1975

[21] Appl. No.: 601,167

Related U.S. Application Data

[62] Division of Ser. No. 408,943, Oct. 23, 1973, Pat. No. 3,921,756.

[52] U.S. Cl. ................................ 181/135; 181/130

[51] Int. Cl.[2] ........................................ A61B 7/02

[58] Field of Search ............................ 181/135, 130

[56] References Cited

UNITED STATES PATENTS

| | | | |
|---|---|---|---|
| 3,602,330 | 8/1971 | Johnson | 181/135 |
| 3,688,863 | 9/1972 | Johnson | 181/135 |

*Primary Examiner*—Stephen J. Tomsky

*Attorney, Agent, or Firm*—Head, Johnson & Chafin

[57] ABSTRACT

This disclosure describes an acoustic ear mold insertable into the ear of an individual with impaired hearing and used in conjunction with a hearing aid. Inserted into the molded portion of the ear mold is a central thin-walled metal tube surrounded by a larger thin-walled metal tube, with annular end plates defining a closed resonance chamber. There is an opening through the wall of the central tube forming a path between the space inside the central tube and the annular chamber. Sound energy from the hearing aid is conducted to the ear mold through the central tube where it is reinforced by resonance in the annular chamber before passing on to the ear of the user.

6 Claims, 8 Drawing Figures

ACOUSTIC EAR MOLD FOR HEARING AID

This is a division of application Ser. No. 408,943 filed Oct. 23, 1973, now U.S. Pat. No. 3,921,756.

CROSS REFERENCE TO RELATED PATENTS

This invention is related to U.S. Pat. No. 3,602,330, issued Aug. 31, 1971, in the name of Rubein V. Johnson, entitled ACOUSTIC EAR MOLD FOR HEARING AID. It is also related to U.S. Pat. No. 3,688,863, patented Sept. 5, 1972, in the name of Rubein V. Johnson, entitled ACOUSTIC EAR MOLD FOR HEARING AID.

BACKGROUND OF THE INVENTION

This invention relates to hearing aids and more particularly to an ear mold for a hearing aid which incorporates a plurality of reflection and resonance chambers. Heretofore, hearing aids have been developed for amplifying sound waves and to conduct the amplified waves to the tympanic membrane of the ear, in order to improve the hearing of an individual. Presently manufactured hearing aid apparatus includes an amplifier, transducer and an ear mold all or parts of which are insertable into the ear.

Amplified sound wave energy created by the amplifier and transducer is usually air conducted to the ear mold, wherein the longitudinal canal or conduit conveys the amplifier sound wave energy to the tympanic membrane of the ear where the normal hearing process is commenced. That is, the sound wave energy strikes the tympanic membrane and then travels onto the malleus, the incus, the stapes, to the oval window and on through the fluid of the inner ear where the cochlea contains the organ of the corti with associated nerve endings of the auditory nerve from the brain.

A disadvantage of the presently manufactured ear molds is that improved hearing is contingent solely upon sound wave amplification. If, for example, otosclerosis has rendered immovable, or partially immovable, the steps due to ankylosis in the oval window, the effectiveness of a hearing aid is lost. Also in many instances where a high level amplification is necessary sound saturation results, whereby the normal process of hearing becomes traumatized and a degree of hearing is not aided insofar as intelligibility is concerned.

In addition to the normal air conduction process of hearing by way of the tympanic membrane, sound wave energy can also be conducted to the hearing part of the brain by means of bone conduction. In bone conduction hearing, vibratory sound wave energy is transmitted to the brain over a separate and distinct route from the normal hearing process. Sound wave energy directly enters the mastoid process and other associated bones of the head and travels by bone conduction to the hearing part of the brain for discrimination and interpretation. Thus bone conduction hearing can be beneficial in reinforcing sound wave energy transmitted to the brain by the normal air conduction process. It is therefore an object of this invention to provide an improved acoustic ear mold for bone conduction of sound wave energy in combination with conventional air born sound wave energy to the ear.

It is another object of this invention to present an improved ear mold wherein amplified sound waves are conducted to the tympanic membrane of the ear and simultaneously therewith to the bones of the mastoid process, and other bones such that sound wave energy is conveyed by two separate routes to the hearing, understanding part of the brain for speech and sound discrimination, interpretation and understanding.

SUMMARY OF THE INVENTION

These and other objects are realized and the limitations of the prior art are overcome in this invention by providing a resonance chamber, a reflection and compression chamber which surrounds the principal tubular channel for acoustical energy transmission from the amplifier and transducer through the ear mold and into the ear. The resonance and reflection chamber is an annular space between the central tubular portion and an outer tubular portion which is closed by annular end plates, to which the central tubular portion is sealed. There is an opening in the wall of the central tube which connects the annular resonance and reflection space with the internal passage or conduit of the ear mold. The outer annular reflection and resonance chamber is confined by the thin walled outer tubing which will vibrate in resonance with the air vibrations in the annular chamber.

This device is molded into the conventional ear mold for insertion into the ear, however, the plastic of the ear mold is of relatively thin wall construction so that no matter how the ear mold is placed in the ear there will be a portion of the vibrating outer tubular wall in relatively close proximity to the bony structure in the mastoid process and other associated bones. Thus, acoustical energy from the transducer that is fed into the ear mold, and through the central tubular portion to the ear, as air carried acoustical energy, is reinforced by the resonance, reflection and compression in the annular chamber to strengthen the acoustical wave being airborn to the ear. Also the resonance reflection and compression in the annular chamber initiates and maintains vibration of the outer tubular wall, and from it through the thin plastic wall of the ear mold and through the tissue of the ear canal into the bony structure of the ear.

In applicant's prior inventions, now U.S. Pat. Nos. 3,602,330 and 3,688,863, there are disclosed improved ear molds which contain reflection and resonance chambers for reinforcing the air conducted sound waves through the central conduit in the ear mold to the tympanic membrane. In one embodiment there is a metallic strip along the edge of the ear mold which is in contact with the reflection chambers so that acoustic energy inside the chambers is communicated to the metal strip along the outside of the ear mold. In U.S. Pat. No. 3,688,863, a second resonance chamber is attached to the outside of the central chamber so that it will be in close proximity to the outer wall of the ear mold and to the bony structure of the ear, to facilitate the transmission of acoustic vibrations through the medium of bone conduction to the brain.

This ear mold is a distinct improvement over both types. The resonance and reflection chamber surrounds the central tubular passage, is enclosed in a thin walled outer cylindrical tube, which vibrates in conjunction with the passage of acoustical energy. Being of selected large diameter the walls of the tube can be placed in close proximity to the bony structure of the ear, irrespective of the orientation of the ear mold inside the ear. Thus there is great convenience in the transmission of vibrations from the outer tubular wall of the device into the body structure of the ear. It is clear, therefore, that this invention has a distinct advantage and is a great improvement over the two prior patents, in that the resonating and reflecting metal surface by means of which vibrational energy is conducted to the bony structure of the ear, is effective no matter what the orientation of the ear mold might be with respect to the mastoid process or other boney structure in the ear. Since it is vibrating on the entire outer surface of the ear mold, it will have a maximum opportunity to communicate the vibrations to bony structure, no matter how associated with the individual ear.

BRIEF DESCRIPTION OF THE DRAWINGS

It is another object of the invention to provide an ear mold for a hearing aid in which a plurality of resonance chambers are provided inside the ear mold for the purpose of filtering and amplifying selected frequencies in the acoustical wave being propagated into the ear through the ear mold, and to provide two paths for transmission of acoustic wave energy from the ear mold to the brain of the user, one of these through the airborn acoustic energy transmitted through the central tube of the ear mold to the tympanic membrane and the other through the vibrating surface of an outer cylindrical metal tube surrounding an annular resonance chamber, the wall of the outer tube being in close proximity to the wall of the ear canal of the user and therefore in close proximity to the bony structure of the ear.

This and other objects of this invention and a clear understanding of the principles and details of the invention will be evident from the following description taken in conjunction with the appended drawings, in which.

DESCRIPTION OF THE PREFERRED EMBODIMENT

Figure 1:
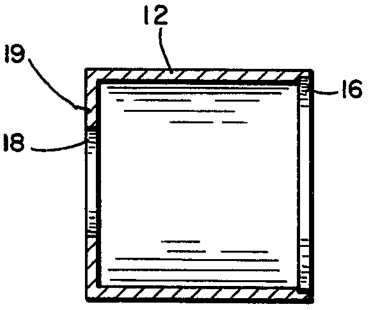
FIGS. 1, 2 and 3 illustrate views of one embodiment of this invention.
Figure 2:
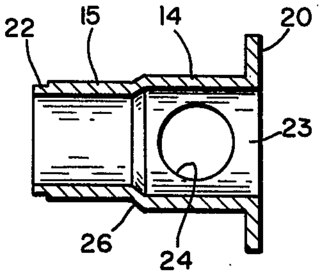
Figure 3:
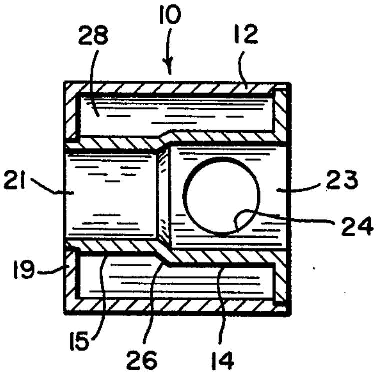

Referring now to the drawings and in particular to FIGS. 1, 2 and 3, there is shown in FIG. 3 the assembly 10 of a metallic reflection and resonance chamber. This is used for reinforcing the resonance and reflection of acoustical energy supplied by a hearing aid amplifying device, for use in a molded ear mold in conjunction with the hearing aid.

FIG. 1 illustrates the outer tubular portion 12 of the device 10 of FIG. 3. The outer portion 12 comprises a thin walled tube with a notch 16 in one end and an annular wall 19 at the other end, with a central opening 18. FIG. 2 shows a central tubular portion of smaller diameter, having two parts 14 and 15 of slightly different diameters, providing an inside and outside angle of incidence for reflection and an inside compression chamber. The larger diameter end 14 faces toward the transducer of the hearing aid, while the smaller diameter end 15 faces toward the ear of the user. There is a flange 20 at the input end 23 which fits into the notch 16 while a notch 22 at the end 21 fits into the opening 18 of outer cylindrical portion 12. When the two parts are inserted one into the other, they can be fastened and the joints sealed by brazing, soldering, spinning, or by similar means.

The assembly product is the end result of different sizes both of inside tubes and also the length of the same, for instance one may be suitable for an individual with an 8 gauge outside tube and a 12 gauge inside tube and may be completed in different lengths, i.e., as 3/16, 4/16, 5/16, 6/16, 7/16, 8/16of an inch. Likewise a combination of a 4 millimeter tube may be used with a thin walled 12 gauge inside tube of different lengths, also, a combination of an outside 5 millimeter tube may be used in conbination with thin walled 10 gauge inside tube of different lengths. All of these combinations are important to make the right type of acoustic mold to more accurately relate to this particular type of hearing loss.

An opening 24 is provided in the wall of the tube 14 to join the space inside the central conduit composed of tubes 14 and 15 with the outer tube 12. All tubes 14, 15 an 12, are thin walled metal preferably noncorrosive metal such as gold, or stainless steel, for example. They are thin enough so that they will resonate in response to the sound vibrations in the chamber 28, for example.

Figure 6:
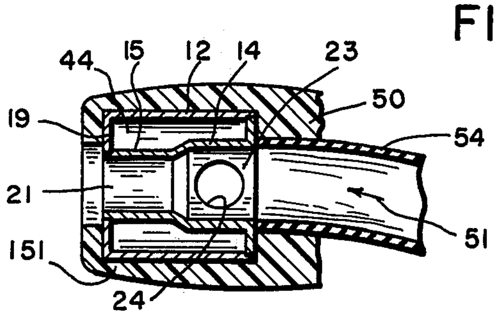
FIG. 6 represents the use of the embodiment of FIG. 1 in a molded ear mold.

Consider now FIG. 6, which is a partial cross section of an ear mold designed for insertion into the ear. The plastic tube 54 leads from the amplifier and transducer of the hearing aid, which supplies acoustical energy in accordance with the arrow 51. This energy enters the opening 23 of the metal device as shown in FIG. 3. Part of the energy goes directly through the tubes 14 and 15 out the end 21, and into the ear of the user, where the airborne acoustic energy strike the tympanic membrane. Part of the acoustical energy is transmitted through the opening 24 in the wall of central tube 14 into the annular space 44, where resonances and reflections are set up, which serve to amplify selected frequency components of the energy moving into the ear mold.

At the same time the outer wall 12 of the device, which is molded into the plastic of the ear mold 50, will vibrate in a radial direction, outwardly and through the thin wall 151 of the plastic of the ear mold, into the wall of the ear canal and bony structure of the ear, where it is transmitted by well known physiological processes to the brain of the user. This bone conduction energy supplements the signals transmitted from the ear of the user responsive to the airborn acoustic energy reaching the tympanic membrane.

In the prior two patents of the present inventor, there was a metallic vibrating surface which was responsive to the acoustical energy passing into the ear mold. However, this metallic surface was of relatively short circumferential extent. In other words, the ear mold had to be positioned in the ear so that this metallic portion was in the proper orientation, to bear against the bony structure of the ear. If the ear mold were to be rotated to another direction where there would not be close enough proximity of the vibrating metal surface to the bony structure, then that path of transmission of acoustical energy to the brain would be lost.

In this invention the vibratory metal surface is cylindrical in shape, and large in diameter, so that no matter what the orientation of the ear mold in the ear canal, there will always be a portion of the vibrating surface in close proximity to that portion of the ear nearest the bony structure. Therefore, there is great assurance that whenever the ear mold is placed in the ear that there will be a vibrating metal surface in close proximity to the bony structure.

Figure 4:
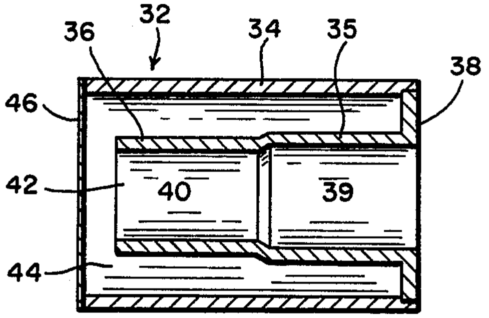
FIGS. 4 and 5 represent a second embodiment of this invention.
Figure 5:
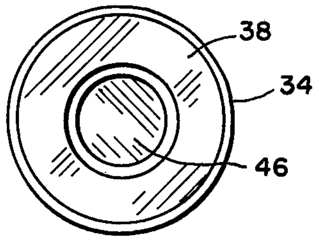

Referring now to FIGS. 4 and 5 there is shown a second embodiment 32 of the improvement of this invention. This, as shown in FIG. 4, utilizes a central tube very similar to a part 14 of FIG. 2, however, there is no opening comparable to the opening 24 through the wall of the central tube 35. Furthermore, the outer tube 34 is not joined by means of an annular wall comparable to element 19 of FIG. 1, which closes the annular space between the outer tube 34 and the inner tubes 35, 36. Instead the outer tube 34 is longer than the inner tubes 35, 36 and is closed off with a very thin diaphragm 46 which is spaced away from the end 42 of the central tube 36. There are thus three resonance chambers 39, 40 and 44 connected to each other.

The embodiment of FIG. 4 differs from that of FIG. 3 in that the air carried vibrations which are transmitted to the tympanic membrane are generated in the ear canal by the vibrations of the thin diaphragm 46. However, like the embodiment of FIG. 3 the outer tubular portion 34 is free to vibrate in response to the pressure oscillations in the annular space 44 and will operate in a similar way to the tubular portion 12 of FIG. 6. Thus the outer tube 34 can transmit vibrations directly to the bony structure of the ear, no matter in what orientation that bony structure may be with respect to the tubular portion 34.

Also in a very mild hearing loss, the sound wave passes through the thin diaphragm 46 on to the ear drum and will greatly reduce traumatic shock by virtue of the sound image being transmitted to the ear drum.

Figure 7:
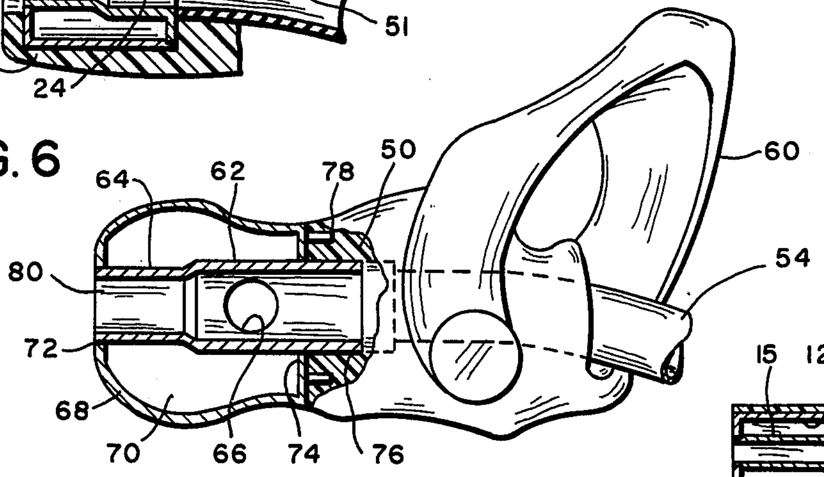
FIG. 7 illustrates a third embodiment of this invention.

In FIG. 7 is shown still a third embodiment of the invention installed on an ear mold, indicated by the numeral 60. This contains a portion 50 which is inserted into the ear. Unlike the drawing of FIG. 6 wherein the metal portions are entirely encased in a plastic coating, identified by numeral 50, in the invention as shown in FIG. 7, there is the same central tubular structure 62 and 64, with an opening, 66 through the wall of the tube 62. Acoustical energy coming by way of tube 54 from the transducer can pass through the central tube 62, 64 and out through opening 80 into the ear and to the tympanic membrane. The outer surface of the ear mold is indicated by numeral 68. This is a thin metal wall shaped in accordance with the desired shape of the ear mold and entirely enclosing an annular space 70 between the central tubes 62, 64 and the outer tubular portion 68. By this means the need for the thin wall of plastic 51 is removed and the vibrating metal surface is in direct contact with the tissue of the ear canal and therefore in closest proximity to the bony structure of the ear.

The metal structure of FIG. 7 may be made removable from the ear mold. For this purpose the central tube 62 has an extension 76 which can be inserted into a corresponding cavity in the molded portion 50 of the ear mold. Two pins 78 are provided to orient the metallic portion with the ear mold 50 so as to maintain the proper orientation for the physical outer contour of the device and to further lock the device into place by use of the serrated pins.

In summary, what has been described comprises a thin walled metallic assembly which contains an inlet opening for the transmission of acoustical energy from the amplifier and transducer of the hearing aid through and into the metallic device, from which acoustical energy is transmitted through the air into the ear and the tympanic membrane, and also through the vibrations of the outer wall of the device to the bony structure of the ear. This device may have a clear central passage through from the inlet to the outlet leading to the ear, or it may have the passage closed by a thin diaphragm. Both designs provide a plurality of reflection and resonance chambers so that by proper design, selected frequencies can be amplified or filtered. The most important advantage of the device, however, is in the provision of a large diameter, thin walled resonance chamber which is in physical contact with the tissues of the ear, canal, or molded into a thin walled plastic covering, but in any case, there is always a portion of this cylindrical metallic vibrator in close proximity to the bony structure of the ear for the transmission of energy through that route to the brain.

While specific details of structure have been shown, these are by way of illustration only, and other details of construction will be evident to one skilled in the art.

Typical dimensions of the metal chambers might be as follows: The wall thickness of the central and outer tubes can be, in the range of 0.005 to 0.010 inches. The inner diameter of the central tube might be in the range of 0.06 to 0.10 inches. The outer diameter might be in the range of 0.13 to 0.25 inches. The length can vary from 3/16 inch to ½ inches in incremental sizes depending on the individual needs. The opening 24 of FIG. 2 is in the range of 0.07 to 0.08 inches. It is possible to make up the total length of the device out of two shorter length devices. Thus, two devices of lengths 3/16 inches and 3/16 inches can be attached (as by soldering), coaxially, end to end, to make a device ⅜ inches long.

The narrowing of the central tube is for the purpose of increasing the intensity of the acoustical energy carried to the ear through the small end. If two devices are attached in series, it is desirable to make the inner diameter of the central tube of the one closest to the ear smaller than the inner diameter of the outermost device, for the purposes of increased intensity.

Figure 8:
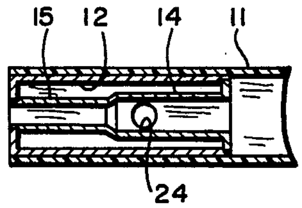
FIG. 8 illustrates a variation of the embodiment of FIG. 3.

The invention may also be used for the transmission of sound to the ear drum without an ear mold, by enclosing the metal tube inside of the tubing 11 that leads from the hearing aid, into the auditory meatus or canal of the ear (see FIG. 8). This is done by preforming the tube 11 to fit into the ear canal, and the metal tube of the device is installed its full length into the tubing itself, pointing toward the ear drum. The use of this preformed tubing (without an ear mold) is being used in the profession of hearing aid fitting where the individual cannot withstand sound level pressure that builds up with an acoustically sealed ear mold.

What is claimed is:

1. In a hearing aid ear mold insertable into the ear canal and having a longitudinal conduit for the passage of sound wave energy from a hearing aid to the tympanic membrane of the ear, the improvement comprising a metal structure having:

a. a central thin walled metal tube forming said conduit, connected at one end by tubular means to said hearing aid, the other end inserted into the ear;

b. an outer thin walled metal tube coaxial with said central tube, and forming an annular space, closed by annular end walls, sealing the space between the ends of said two tubes;

c. an opening in the wall of said central tube, joining said annular space and the space inside said conduit;

d. and wherein said outer tube is of a diameter and shape to snugly fit the ear canal whereby vibration of said outer tube is communicated directly to the auditory meatus and to the bony structure of the ear.

2. An ear mold of claim 1 including a plastic member affixed to one end of said tubes and contoured to fit the ear of the user and having a passageway therein communicating with said conduit and receiving said tubular means.

3. An ear mold of claim 1 in which said central tube is constructed with two portions of different diameters.

4. An ear mold of claim 3 in which the portion of larger diameter is connected to the hearing aid tubular means.

5. An ear mold of claim 3 in which said opening in the wall of said central tube is in the portion of larger diameter.

6. An ear mold of claim 1 in which said outer tube is made of a metal selected from gold and stainless steel.

* * * * *